United States Patent [19]

Bae

[11] Patent Number: 5,583,902
[45] Date of Patent: Dec. 10, 1996

[54] METHOD OF AND APPARATUS FOR PREDICTING COMPUTED TOMOGRAPHY CONTRAST ENHANCEMENT

[75] Inventor: Kyongtae T. Bae, St. Louis, Mo.

[73] Assignee: BHB General Partnership, St. Louis, Mo.

[21] Appl. No.: 539,859

[22] Filed: Oct. 6, 1995

[51] Int. Cl.$^6$ .................................................. A61B 6/03
[52] U.S. Cl. ........................... 378/8; 378/95; 364/413.15
[58] Field of Search ........................ 364/413.14, 413.15; 378/210, 4, 8, 95, 98.9, 98.11, 98.12, 901

[56] References Cited

U.S. PATENT DOCUMENTS

| | | | |
|---|---|---|---|
| 5,034,987 | 7/1991 | Fujimoto et al. | 382/6 |
| 5,383,231 | 1/1995 | Yamagishi | 378/15 |
| 5,459,769 | 10/1995 | Brown | 378/4 |

OTHER PUBLICATIONS

Dynamic Hepatic CT: How Many Years Will It Take 'Til We Learn'? Walkey, M. M. *Radiology*, vol. 1, Oct., 1991: 181–17–24.

Investigation of Contrast Enhancement In CT Of The Liver: The Need For Improved Methods, Dodd, G. D., Baron, R. L. (commentary), *AJR* 1993: 160:643–646.

Contrast–Enhanced Spiral CT Of The Liver: Effect Of Different Amounts And Injection Rates Of Contrast Material On Early Contrast Enhancement. Small, W. C., Nelson, R. C., Bernardino, M. E., Brummer, L. T. *AJR* 1994: 163:87–92.

Cardiac Output And Regional Blood Flow, Wade O. L., Bishop, J. M. F. A. Davis Co., Philadelphia, 1962, pp. 86–95.

Cardiovascular Physiology. Milnor, W. R. *Oxford University Press*, Oxford, 1990, pp. 6–13; 28–39; 52–59; 328–331; 436–445.

Structure–Function Relations In The Peripheral Circulation. *Best & Best & Taylor's Physiological Basis of Medical Practice*, Twelfth Edition, Chapter 6, pp. 118–123; 128–130; and 142; Chapter 25, Physiology Of The Body Fluids, pp. 406–408, edited by West, J. B., Williams & Wilkins, 1991.

Circulation–Time Models Of The Uptake Of Inhaled Anaesthetics And Data For Quantifying Them. Mapleson, W. W. *Brit J. Anaesth*, 1973; 45:319–333.

Summary of Organ Weight (g) For Pediatric And Adult Phantoms, *CRC Handbook of Medical Physics*, ICRP Publication 23, 1984, pp. 428, 134–135.

(List continued on next page.)

Primary Examiner—David P. Porta
Assistant Examiner—David Vernon Bruce
Attorney, Agent, or Firm—Howell & Haferkamp, L.C.

[57] ABSTRACT

A method and apparatus are disclosed for predicting prior to injection an organ specific contrast enhancement in a patient for a preselected contrast injection protocol for pre-determining a computed tomography scan. The invention is preferably implemented in a computer program which creates a mathematical model of human cardiovascular physiology in a hypothetical patient with a specific body habitus subjected to the pre-selected contrast injection protocol. The predicted contrast enhancement is then displayed for operator approval and may be then used to control a CT scanner to perform the scan with the pre-selected injection protocol. The mathematical model includes models of organs and vessels using differential equations to describe mass transport of contrast agent through the cardiovascular system.

22 Claims, 12 Drawing Sheets

OTHER PUBLICATIONS

Local Control Of Blood Flow By The Tissues And Nervous And Humoral Regulation, Textbook Of Medical Physiology, Chapter 20, Guyton, A. C. W B Saunders Co. 7th Ed. Philadelphia, 1986, pp. 228, 230, 340, 342, Chapter 33, Partition of The Body Fluids: Osmotic Equilibria Between Exctracellular And Intracellular Fluids, pp. 382, 384, 386, 388, 390, and 392.

Human Pharmacokinetics Of Iohexol: A New Nonionic Contrast Medium. Olsson, B. Aulie A, Sveen, K., Andrew, E. *Investigative Radiology* Mar.–Apr. 1983; vol. 18, 18:177–182.

Applications Of A Mathematical Model For Drug Distribution In Mammals In Chemical Engineering In Medicine And biology. Bischoff, K. B. Edited by D. Hershey, Plenum Press, NY, 1967;417–466.

Transport Phenomena In The Cardiovascular System, Middleman, S. *John Wiley & Sons, Inc.* NY, 1972, pp. 1–299.

Radioisotopes And Circulation, Nadler S. B., Hidalgo J. U. *Little, Brown & Co.,* Blood Volume, Ch. 4, Boston 1965, pp. 64–71, 86–93.

Numerical Recipes. Chapter 15, Integration of Ordinary Differential Equations. Press WH, Flannery B. P., Teukolsy S. A., Vetterling W. T., *Cambridge University Press,* Cambridge, 1986, pp. 547–561.

Dynamic Contrast–Enhanced CT Of The Liver: Comparison Of Contrast Medium Injection Rates And Uniphasic And Biphasic Injection Protocols. Heiken J. P, Brink J. A., McClennan B. L., Sagel S. S., Forman H. P., DiCroce J. *Radiology* May, 1993; 187:327–331.

Dynamic Incremental CT: Effect Of Volume And Concentration of Contrast Material And Patient Weight On Hepatic Enhancement. Heiken J. P., Brink J. A., McClennan B. L., Sagel S. S., Crowe T. M., Gaines M. V. *Radiology,* May, 1995; 195:353–357.

Extravascular Contrast Material: The Major Component Of Contrast Enhancement. Kormano M, Dean P. B. *Radiology.* Nov., 1976; 121:379–382.

The Permeability Of Capillaries In Various Organs As Determined by Use Of The 'Indicator Diffusion' Method. Crone, C. *Acta Physiol Scand* 1963; 58:292–305.

Estimation Of The Capillary Permeability Coefficients Of Inulin In Various Tissues Of The Rabbit. Wittmere L. E., Bartlett M., Johnson J. A. *Microvas Res* 1976; 11:67–78.

A Linear Method For Determining Liver Sinusoidal And Extravascular Volumes. Goresky C. A. *American Journal Physiology.* 1963;204(4):626–640.

Capillary Exchange Modeling: Barrier–Limited And Flow––Limited Distribution. Goresky C. A., Ziegler W. H., Bach G. G. *Circulation Research* Nov., 1970;27:739–764.

Some Mathematical Aspects Of Chemotherapy–II: The Distribution Of A Drug In The Body. Bellman R., Jacquez J. A., Kalaba R. *Bull Math Biophys.* 1960;22:309–322.

Respiration And Circulation, Altman P. L., Dittmer D. S. *Federation of American Society of Experimental Biology,* Bethesda, M. D., 1971, pp. 227, 232, 234, 320, 357, 377, 379, 383, 385, 417, 419, 424, 426, 428, 431, 433, 435, 459, 501, 503, 505, 507, 510.

Radiopapque Contrast Media Radiopharmaceuticals Enhancement Agents For Magnetic Resonance Imaging And Ultrasound. Swanson D. P., Weingarden M. Swanson D. P., Chilton H. M., Trall J. H., ed. *Pharmaceuticals In Medical Imaging.* Macmillan Pub. Co. NY, 1990, pp. 78–97.

Circulatory Physiology: Cardiac Output And Its Regulation. Guyton A. C. W. B. Saunders Co., Philadelphia, 1963, pp. 3–15, 154–157.

Changes In Cardiac Output With Age. Brandfonbrener M. et al. Circulation vol. 12, Oct. 1955, pp. 557–566.

Measurement Of Cardiace Output by Computed Transmission Of Tomography. Herfkens R. J., et al. Inv. Radiology Nov.–Dec., 1982, pp. 550–553.

Dynamic Contrast Enhancement Of The Upper Abdomen: Effect Of Contrast Medium And Body Weight. Kormano, M., M. D., Kaarina P., M. D., Soimakallio, S., M. D. Kivimaki, T., R. T. *Investigative Radiology,* vol. 18, Jul.–Aug. 1983, pp. 364–367.

Helical CT of the Liver: Clinical Application of An Automated Computer Technique SmartPrep for Obtaining Images With Optimal Contrast Enhancement; Silverman P., Roberts S., Tefft M. C., Brown B., Fox SH., Cooper C., Zeman R. *AJR* Jul., 1995 165:73–78.

Optimal Contrast Enhancement Of the Liver Using Helical (Spiral) CT: Value of SmartPrep. Silverman P., Brown B., Wray H., Fox S., Cooper C., Roberts S., Zeman R. *AJR* May, 1995; 164:1169–1171.

Technical Developments and Instrumentation. Parenchymal Liver Enhancement With Bolus–Triggered Helical CT: Preliminary Clinical Results. Kopka L., Funke M., Fischer U., Vosshenrich R., Oestmann J. W., Grabbe E. *Radiology* Apr., 1995, vol. 195, No. 1, pp. 282–284.

Enhancement (H.U.)

| TIME (MIN.) | AORTIC | HEPATIC |
|---:|---:|---:|
| 0 | 0 | 0 |
| 0.13 | 16.23 | 0.02 |
| 0.25 | 187.3 | 3.12 |
| 0.38 | 285.65 | 15.53 |
| 0.51 | 324.22 | 34.8 |
| 0.64 | 176.9 | 52.39 |
| 0.77 | 135.62 | 60.29 |
| 0.91 | 127.09 | 62.9 |
| 1.04 | 127.15 | 63.57 |
| 1.17 | 122.31 | 63.57 |
| 1.3 | 114.23 | 63 |
| 1.43 | 108.87 | 61.84 |
| 1.56 | 106.65 | 60.38 |
| 1.69 | 104.54 | 58.93 |
| 1.82 | 100.87 | 57.47 |
| 1.95 | 96.48 | 56 |
| 2.07 | 92.46 | 54.45 |
| 2.2 | 89.1 | 52.81 |
| 2.34 | 86.21 | 51.15 |
| 2.47 | 83.57 | 49.55 |
| 2.59 | 81.09 | 48.04 |
| 2.73 | 78.65 | 46.51 |
| 2.85 | 76.5 | 45.11 |
| 2.98 | 74.49 | 43.79 |
| 3.11 | 72.56 | 42.51 |
| 3.23 | 70.72 | 41.29 |
| 3.37 | 68.93 | 40.1 |
| 3.49 | 67.25 | 38.97 |
| 3.63 | 65.63 | 37.87 |
| 3.75 | 64.17 | 36.87 |
| 3.88 | 62.78 | 35.93 |
| 4.01 | 61.45 | 35.01 |
| 4.14 | 60.21 | 34.16 |
| 4.27 | 58.99 | 33.32 |
| 4.4 | 57.83 | 32.52 |
| 4.52 | 56.75 | 31.78 |
| 4.65 | 55.75 | 31.1 |
| 4.78 | 54.79 | 30.44 |
| 4.9 | 53.85 | 29.79 |
| 5 | 53.18 | 29.34 |

FIG. 15

METHOD OF AND APPARATUS FOR PREDICTING COMPUTED TOMOGRAPHY CONTRAST ENHANCEMENT

FIELD OF THE INVENTION

This invention relates generally to an apparatus and method for predicting organ specific contrast enhancement prior to computed tomography scanning of a patient. Specifically, this invention relates to a computer simulation of contrast agent transport throughout the body to predict organ specific enhancement in patients of variable height and weight subjected to various contrast injection protocols to enable operator selection of an appropriate injection protocol prior to commencing the scan.

BACKGROUND OF THE INVENTION

Computed tomography (CT) is a widespread diagnostic imaging method which measures the x-ray attenuation coefficient of matter. This x-ray attenuation coefficient is depicted in terms of Housefield Units (HU). During a CT scan, a collimated X-ray beam is directed on the patient and the attenuated remnant radiation is measured by a detector whose response is transmitted to a computer. The computer considers the location of the patient and the spatial relationship of the x-ray beam to the region of interest. The computer analyzes the signal from the detector so that a visual image can be reconstructed and displayed on a monitor. The image can then be viewed or stored for later evaluation.

Housefields Units reflect the relative absorption of CT x-rays by matter, the absorption being related to the atomic number, electron density, physical thickness of that matter, and the energy spectrum of the x-rays. Because of the similarity in electron density of various tissues in the body, CT scans sometimes result in poor imaging. In an attempt to obtain better results in such circumstances, a contrast agent, such as iodine, can be injected in the patent's blood stream to change the relative radio-density of the tissues, and improve overall diagnostic efficacy.

When using a contrast agent, it is extremely important to coordinate the time of the scan with the time of greatest levels of contrast in the region of interest, in some instances with respect to a threshold value. Because the contrast agent is injected into the blood stream, many physiological factors can affect the start time and duration of a sufficient level of contrast in the region of interest. For example, because the cardiovascular system provides the means for circulation of contrast agent throughout the body after it is injected into the blood stream, a patient's cardiac output can have a significant effect on the distribution of the contrast agent as well as the time taken for the contrast agent to reach a particular organ or vessel.

Current understanding of intravenous contrast enhancement is further complicated by multiple interacting factors including contrast agent type, volume and concentration, injection technique, catheter size and site, scanning technique, patient characteristics and tissue characteristics. Of these factors, all of which have influence on contrast enhancement, the variables which cannot be controlled are those related to the patient. These include age, gender, weight, height, cardiovascular status, renal function and other disease status. In the past ten years, many clinical studies testing various intravascular contrast agent and injection protocols have been reported. However, in many respects, contrast enhancement still relies heavily on the experience and intuition of the physician rather than rigorous, quantitative analysis of the mechanism of contrast enhancement.

SUMMARY OF THE INVENTION

The present invention provides a method of and an apparatus for predicting tissue specific CT contrast enhancement in a patient with a specific body habitus subjected to different contrast injection protocols. The method is preferredly implemented in a computer program, and the computer itself may be used to also control the CT scan in accordance with an operator's choice. Such a physiological model of contrast enhancement has many potential clinical applications.

The present invention utilizes a compartmental model of the human cardiovascular system and assigns differential equations describing mass transport to each compartment of the model. Regional circulation parameters such as blood volume, regional blood flow and extracellular fluid volume were estimated using available data to provide input to the equations. Local tissue structures such as organs and vessels were modeled mathematically to describe the distribution and dispersion of an intravascularly-administered contrast agent. A global model was then formed by integrating the regional circulation parameters with the models of local tissue structures.

The present invention, which is preferably implemented in a computer program, allows an accurate prediction of the time varying distribution and concentration of contrast in the body. This in turn allows an operator to predict the time and duration of maximum enhancement in a specific organ or tissue in a patient for a particular injection protocol. Most importantly, the operator can use the present invention to predict the time a scan should be started and the duration of the scan based on output data from the program. This output can take the form of a data stream or can be a graph of contrast enhancement, versus time. With more advanced generations of CT machines, such as spiral and helical CT scanners as are known in the art, a typical scanning procedure can be completed within approximately 30 seconds. The present invention enables an operator to choose an injection protocol to ensure that the entire scan take place during a period of maximum enhancement, and while enhancement exceeds a suitable threshold.

In the prior art, there are devices which monitor and output contrast enhancement levels for a region of interest. Using these prior art devices, an operator injects the contrast agent, views the output, and determines when to begin a scan based on when the enhancement level attained in the region of interest becomes acceptable. The prior art devices require the injection of the contrast agent and low dose x-rays of the region of interest. For example, in the prior art, the injection of a contrast agent is started and the prior art device monitors at regular intervals the enhancement level in the region of interest and provides an output. The operator can view the output and then decide when to begin the scan.

The present invention is an improvement over the prior art in that it allows prediction of contrast enhancement levels and duration of those enhancement levels prior to injection of the contrast agent and without the need of low dose X-rays. Moreover, because different injection variables, such as rate and concentration, can alter the enhancement levels, the present invention allows calculation of various alternatives to choose the best injection scheme for a particular patient.

The prior art device also does not reveal if the required enhancement threshold level will ever be attained. Thus, using the prior art device, an operator does not know if the required level will be reached until after a full scan. This is particularly important for scans of certain tissues whose contrast enhancement behavior is complex, as explained in greater detail below.

The present invention also allows an operator to adjust the collimation or slice thickness and CT table speed to optimize a scan. During a CT scan, a patient lies on a table which moves through the CT scanner from head to toe vertically, and over the selected region of interest. The collimation or slice thickness is the thickness of the slice of the patient's body that is transaxially scanned. The table can usually be moved at a rate per second of up to two times the collimation thickness. Using the present invention, an operator can optimize the collimation rate and table speed. For example, if there is a limited period of threshold enhancement, the operator knows that an increased table speed or an increased collimation thickness must be used to ensure that the entire scan is completed during the period of maximum enhancement. Customizing the scan is less precise with the prior art.

The present invention can be implemented in many ways including a separate computer or a CT machine with the present invention integrated with the controls. The present invention is capable of using standard values for variables which influence enhancement levels and also allows input of patient specific values. For example, a particular patient habitus may be such that the standard values for variables such as blood volume, blood flow etc., will not provide an accurate prediction of enhancement levels. The present invention utilizes several methods to resolve such situations. One method provides for the input of patient specific information to customize the operation to the particular patient. This includes patient specific variables such as weight, age, height and gender. These variables can be measured and input to adjust the standard variables accordingly.

On occasion, other variables which are not readily measurable may need to be modified. As is well known in the art, cardiac output cannot be measured as readily as height or weight. Of course, a patient with a known history of heart failure or increased age will most certainly have a cardiac output below normal. If this is the case, the present invention allows adjustment of the standard variables accordingly.

Another aspect of the method in the present invention allows the operator to choose several alternative values for cardiac output and generate a family of predicted enhancement curves for each value. After injection of contrast agent is started, actual measurements of enhancement can be compared to the initial portions of the family of curves to determine which family member most closely resembles the actual results. In this way, early in the scan and before the threshold has been reached, a choice of which curve to utilize to best predict when the scan should occur can be made. This choice can be made by the operator or automatically by the computer.

The present invention has particular application where the organ or vessel being scanned is incapable of maintaining threshold enhancement levels for a sustained period. One such example is CT angiography. In CT angiography, a CT scan is taken of a blood vessel or vessels. Unlike organs, blood vessels do not maintain high enhancement levels over time and the timing of the scan is critical. CT angiography is performed in the prior art by injecting a test dose of contrast agent and measuring with low dose x-rays the elapsed time for the contrast agent to reach the region of interest. Thereafter, a full dose of contrast agent is injected and a scan is initiated after lapse of the previously measured time delay. However, there is no guarantee of a particular enhancement level being attained or sustained as required to achieve a successful scan. Using the present invention, one can more accurately predict not only the time delay, but also the degree of enhancement and its duration.

While the principal advantages and features of the invention have been described above, a greater understanding of the invention may be attained by referring to the drawings and the description of the preferred embodiment which follow.

BRIEF DESCRIPTION OF THE DRAWINGS

FIG. 15 is a data stream output generated by the present invention showing predicted aortic and hepatic enhancement levels in a hypothetical patient with standard blood volume and standard cardiac output using uniphasic-high flow rate injection protocol in Table Six.

DETAILED DESCRIPTION OF THE PREFERRED EMBODIMENT

Figure 1:
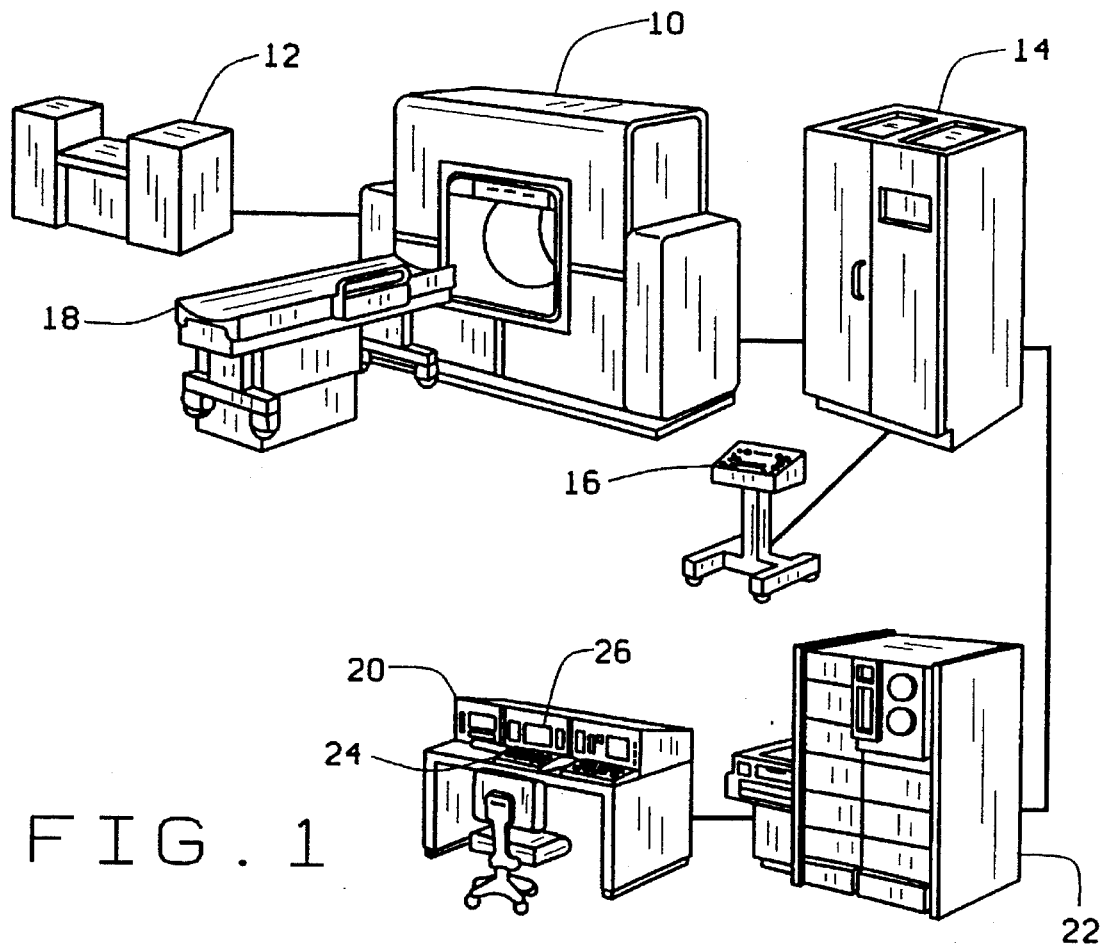
FIG. 1 is a diagram showing the components of a complete CT scanner system and a computer control console.

Computed Tomographic (CT) scanning is an invaluable radiologic diagnostic tool. The major components of a conventional CT scanner are shown in FIG. 1. The CT scanner 10 contains the x-ray tube and detector array. Power is supplied by a high voltage generator 12 controlled by scanner electronics 14 and scanner service module 16. The patient support and positioning couch 18 is moveable to transport the patient through the scanner 10. The scanner 10 and voltage generator 12 receive electronic commands from the operating console 20 and transmit data to the computer system 22 for image production and analysis. The operating console 20 usually contains an interactive keyboard 24 and CRT monitor 26.

In the preferred embodiment, the present invention is implemented in a computer program. As most CT scanners utilize computers to control the operation of the scanner, the present invention could be easily integrated therewith. In that fashion, the operator could run the program prior to the scan and the computer can determine the optimum scan parameters and using the determined values complete the scan accordingly. In this way, the CT scan computer can determine as well as implement the scan parameters. In the alternative, a separate computer which contains the program could be utilized. The scan parameters could be determined by running the program in the separate computer and then input into the CT scan computer by the operator or through computer data transfer methods.

Figure 2:
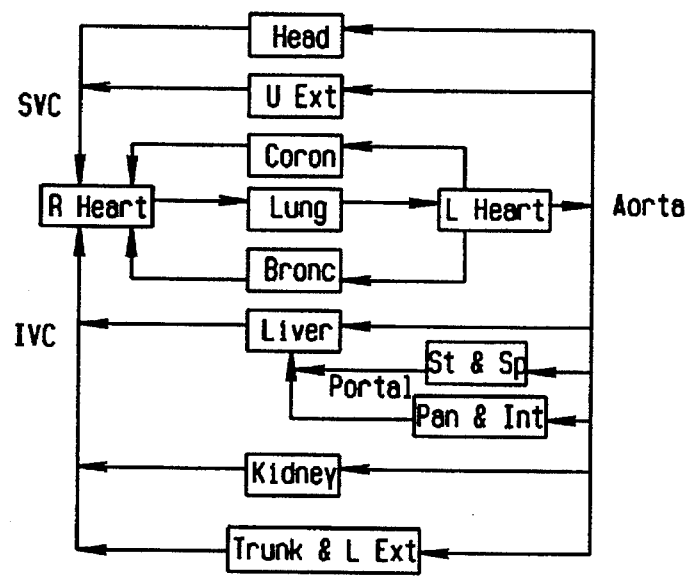
FIG. 2 is a schematic diagram of the major organs of a human cardiovascular circulation system.

The present invention utilizes a model of the human cardiovascular system to describe mass transport of contrast agent throughout the body. The cardiovascular system provides the means for circulation of contrast agent throughout the body after it is injected into the bloodstream. The human cardiovascular system is very complex and has numerous controlling mechanisms, including neuronal, hormonal and psychological controls. A simplified human cardiovascular system as shown schematically in FIG. 2 consists of the heart, vascular networks, and key organs which serve as reservoirs. Normal blood volume and flow distribution throughout the body are well established in the prior art and are given in the Tables 1 and 2 (All Tables are shown in Exhibit A attached hereto and incorporated herein by reference).

Based on well known information, the preferred embodiment assumed that the average blood volume was 5 liters. This includes 3 liters of plasma and 2 liters of red blood cells. The average cardiac output was also estimated from known sources to be 6.5 liters per minute. These values were used to describe a standard model of the cardiovascular system. However, the preferred embodiment allows these values to be adjusted according to the patient's age, gender, weight and height using standard nomograms outlined below.

Because contrast agent diffuses passively from the bloodstream across the capillary membrane into the extravascular space, the distribution of fluid throughout the body was included in the cardiovascular model. The amount of total body water (TBW) in an adult of average weight (70 Kg) was assumed to be 40 L. TBW was divided into two major components, intracellular fluid (ICF) and extracellular fluid (ECF). The ECF was further divided into several smaller compartments including interstitial fluid, plasma, and cerebrospinal fluid. The interstitial fluid is the largest compartment and lies in the lymphatics and the spaces between cells.

The ECF volume is usually estimated with dilution methods in which a substance is injected into the blood stream and diffuses throughout the entire extracellular fluid compartment with little entering into the cells. However, an ideal substance for such dilution studies has not been identified, and measurements for a 70 kg adult have ranged from 9 L to 22 L depending on the substances used. The size of the measured ECF decreases with increasing the molecular weight of the substance used. The apparent volume distribution of iohexol has been reported to be 0.27 l/kg. Thus, for a 70 Kg adult, this equates to an ECF of 18.9 L. In the preferred embodiment this value for ECF volume was used which includes a plasma volume of 3.0 L. The overall estimated distribution of body fluid used in the cardiovascular model is summarized in Table 3.

The detailed distribution of fluid in a local organ was estimated from the standard mass of an organ and its water content. The volume of the total systemic capillary bed is estimated to be about 300 ml. However, a detailed breakdown of capillary volumes in different regions is not available. In addition, the number of capillaries within an organ varies considerably from one organ to another. It is believed that the regional capillary volume is directly proportional to a regional blood flow and the preferred embodiment cardiovascular model applied this assumption. These values are likely overestimated in highly perfused organs such as the kidney and the liver but this did not hinder the performance of the model. Table 4 shows the regional capillary volumes in the systemic circulation estimated from the regional blood flow values given in Table 2.

A calculation of the regional distribution of the extracellular and intracellular fluid was also necessary for the present invention. The regional distribution of total body fluid can be calculated from the known mass of each organ and its water content, assuming a density of 1.0 g/mL. The weight and percent of water content of the visceral organs are shown in Table 5 along with their total fluid value minus the capillary volume. Without available information, the preferred embodiment assumes 70% water content in the stomach, spleen and intestine. The lung consists of 50% parenchyma and 50% nonparenchyma tissues whose capillary volumes are 150 mL and 5 mL, respectively.

The total body fluid of the upper extremities, trunk, and lower extremities was calculated by subtracting from the total body water volume (40 L), the blood volume (5 L), and the total fluid of the visceral organs minus the capillaries (4,726 mL). The mass ratio of the lower extremities and trunk to the upper extremities is about 4:1. Thus, the total body fluid of the upper extremities becomes 6,055 mL and that of the lower extremities and trunk, 24,219 mL.

Table 3 shows the overall volumes of ICF fluid and ECF fluid as 19.1 L and 15.9 L. respectively. However, regional distribution of the ICF and ECF is not shown. Some tissues such as the skin, adipose tissue, G-I tract, and liver have larger extracellular to intracellular fluid ratios than, for example, muscle. As no data regarding such fluid ratios are available, in the preferred embodiment it was assumed the ratio of ECF to ICF to be the same in all body regions. For example, the ECF and ICF volumes of the liver were estimated as 524 and 629 mL respectively.

After regional blood flow, blood volume, and distribution of body fluid were estimated, local structures were modeled mathematically to describe the distribution and dispersion of intravascularly administered iodinated contrast agent within local regions. The blood vessels are viscoelastic with complex mechanical properties to accommodate pulsatile blood flow and various pressure gradients. Although the blood flow in large vessels is generally streamlined, some mixing occurs within the blood vessel because of molecular diffusion, flow pulsability and convections at multiple branching points. The dispersion may be even greater in smaller and low pressure vessels. To simplify the model, blood vessels were represented as rigid structures without directly incorporating their dynamic pulsatile properties in the preferred embodiment.

A blood vessel could be analyzed in the cardiovascular model as a simple conduit without any longitudinal mixing. This is known in the art as "plug flow." In this type of model, each artery and vein is divided into segments, and blood enters as plugs each heartbeat and displaces an equal volume of blood without any longitudinal mixing. The major problem with this approach is excessive demands on computer memory required to store the history of each segment throughout the circulation. An alternative approach is to consider a blood vessel as a well-stirred compartment or well-mixed pool of blood. This approach simplifies computation, requires far less computer storage and has been shown to perform as well as the plug flow model in the prior art. Thus, in the preferred embodiment cardiovascular model the heart and blood vessels were analyzed as well-stirred compartments.

Figure 3A:
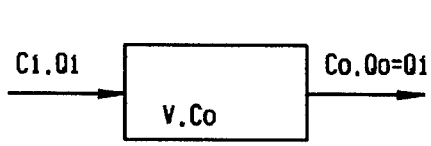
FIG. 3(a) is a block diagram of a single well stirred compartment with an input having a constant input concentration $C_i$ and input flow rate $Q_i$, the compartment having a volume V and an output with a concentration $C_o$ and an output flow rate $Q_o$.

A single, well-stirred compartment contains a constant volume, V, with a single inlet flow and a single outlet flow as shown in FIG. 3(a). $Q_i$ and $Q_o$ represent the input and output volumetric flow rates of the blood, respectively. The input and output flow rates are the same in a constant volume compartment ($Q=Q_i=Q_o$). $C_i$ and $C_o$ represent the input and output concentrations of contrast agent, respectively. Since we assume the compartment to be well mixed, the concentration within the compartment is the same as that of the output. A mass balance of the concentration is described by Fick's Principle, shown schematically in FIGS. 3(a) and 3(b) in the following equation:

$$V*dCo/dt=Q(C_i-C_o).$$

Figure 3B:
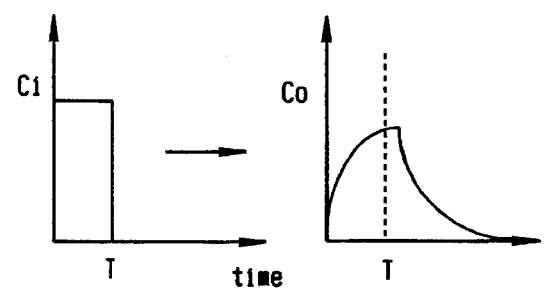
FIG. 3(b) is a graph of the input concentration of the input in FIG. 3(a) and a graph of the corresponding output concentration $C_o$ over time.

For a given volume, V, a given volumetric flow rate Q, and a given input concentration, $C_i$, we can estimate the output concentration, $C_o$, by solving this differential equation. The net effect of a well mixed compartment is to disperse the input concentration over the compartment resulting in more broadly distributed output concentration over time. For constant flow rate, Q over a fixed time interval, T, the input concentration given as a step function is mathematically transformed to the output concentration curve as shown in FIG. 3(b). The transformation is described mathematically as two exponential functions of V, Q and T. The output concentration curve is broader temporally than the input concentration curve, and a central peak is present.

Modeling an organ is more complex than modeling a blood vessel because the contrast agent is no longer confined in the intravascular space and permeates through the capillary membrane into the extravascular space. The simplest approach to modeling an organ is to assume that it also is a well-stirred compartment. However, the single compartment organ model does not address differences in the exchange of contrast agent along subcompartments within an organ and is limited in describing the behavior of substances with different transcapillary permeabilities. A common alternative approach used in the prior art to investigate the distribution of chemotherapeutic agents throughout the body involves splitting each organ into three well known spaces: the capillary or intravascular space (IV), the extracellular space (EC), and the intracellular space (IC). This is shown schematically in FIG. 4(a). For a given organ, each of these three spaces was modeled as a single, well-mixed compartment. Diffusion through membranes, either active or passive, permits exchange of substances along the spaces within the organ. However, because iodinated contrast agent does not penetrate into the cells, only the intravascular (IV) and extracellular (EC) compartments were considered and the intracellular (IC) compartment was ignored.

Figures 4A, 4B:
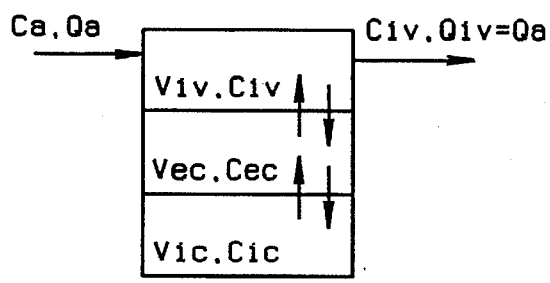
FIG. 4(a) is a block diagram of an organ modeled in three spaces: intravascular (IV), extracellular (EC), and intracellular (IC)
FIG. 4(b) is a block diagram of the IV and EC spaces of FIG. 4(a) detailing the mass transfer rate (dM/dt) therebetween.

Transcapillary exchange of substances between the intravascular and extracellular compartments can be described by Fick's Law of Diffusion and is shown schematically in FIGS. 4(a) and 4(b). The mass transfer rate (dM/dt) is proportional to the diffusion coefficient (D), the surface area (S), and the concentration difference ($C_i-C_o$) for a given membrane thickness (dX) as represented by the following equation:

$$dM/dt=DS(C_i-C_o)/dX.$$

For a thin membrane, the mass transfer rate is simpler such that permeability (P) is commonly used to combine D and dX as a unit resulting in the following equation:

$$dM/dt=PS(C_i-C_o)$$

To complete the mathematical model, two governing differential equations were applied to each organ. One for the intravascular space and the other for the extracellular space. The intravascular space had two transport components. The first component was obtained from blood flow related mass balance, i.e., the inflow of contrast agent minus the outflow. The second component was obtained from the mass balance related to the transcapillary exchange within the extracellular space. For the extracellular space, only one transport component was considered: the mass balance related to transcapillary exchange with the intravascular space. These equations are as follows:

$$V_{iv}*dC_{iv}/dt=q(C_i-C_{iv})-PS(C_i-C_{ec})$$

$$V_{ec}*dC_{ec}/dt=PS(C_{iv}-C_{ec})$$

Figure 5:
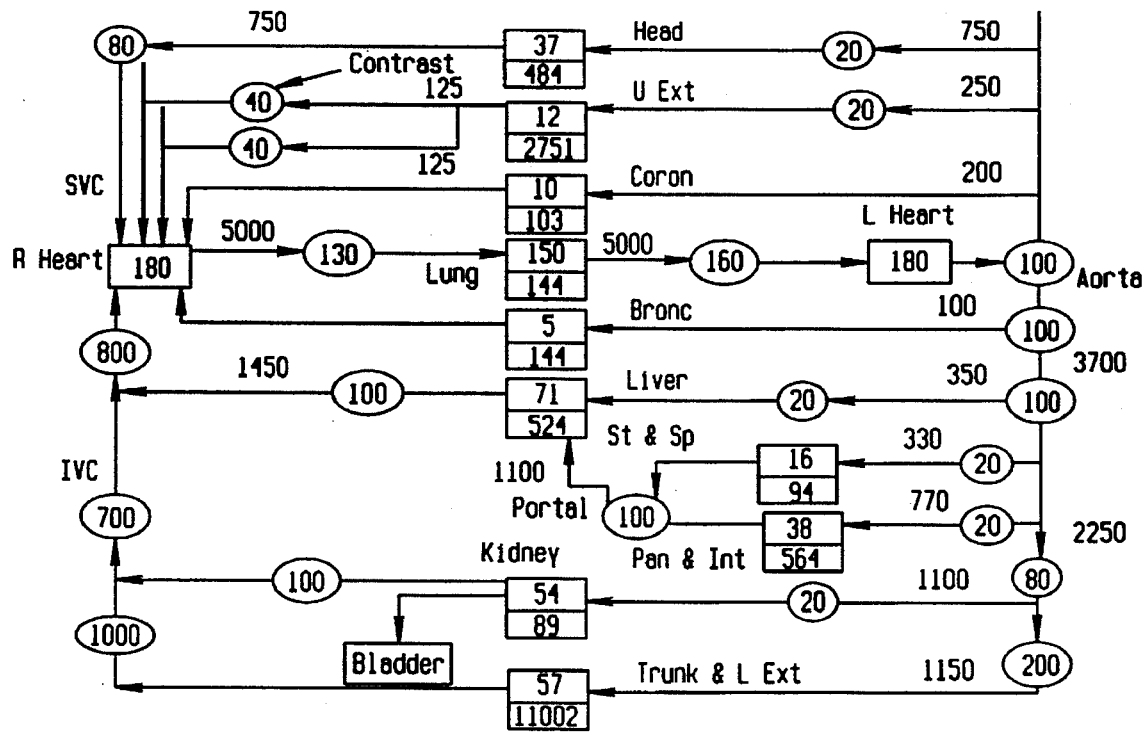
FIG. 5 is a block diagram of the global cardiovascular model of the body.

The global model, shown schematically in FIG. 5, was formed by integrating the regional circulation parameters with the models of local regions. In the preferred embodiment, contrast agent was assumed to be injected through an antecubital vein, mixed in the right heart, distributed throughout the body and excreted by the kidneys according to the glomerular filtration rate.

The residence time of contrast agent in an organ was estimated by the time duration of the contrast agent in the capillaries and ECF spaces. The residence time depends on the size of these spaces as well as the transcapillary exchange rate. When a substance is confined to a blood vessel, the circulation time is measured by injecting rapidly a dye or radioactive tracer into a peripheral vein and detecting the moment when it arrives at a sampling site. The volume of a blood vessel travelled by a substance is calculated by multiplying the volumetric flow rate and the circulation time. The mean circulation time from the antecubital vein to the right atrium is approximately 6.9 seconds in an average adult. The time can range from 3 to 14 seconds. This is the temporal difference between the antecubital and the right atrial injections.

Intravascular contrast agents are eliminated from the body mainly by the kidneys. The process is rapid with approximately 50% of injected contrast agent being excreted within two hours presuming normal renal function. The total excretion rate of contrast agent is obtained by multiplying the plasma concentration with a glomerular filtration rate, usually about 19% of renal plasma flow. Peak renal excretion is closely related to peak plasma concentration, because renal plasma flow is relatively constant.

Regional blood flow is expressed according to the magnitude and direction of the flow. For example, the cardiac output is 6500 mL/min., directed away from the right heart. In FIG. 5, the right and left heart are represented by boxes by denoting well stirred compartments. Each blood vessel is represented by a circle surrounding a number which represents its volume in milliliters. Large blood vessels are further divided into multiple smaller compartments in series, typically 20 mL for arteries, and 100 mL for veins: the volume of systemic veins is about 4 to 5 times that of associated arteries. This division scheme in large vessels is rather arbitrary and was based on computational convenience. However, the total blood volume in a given blood vessel closely followed known physiological values.

In FIG. 5, each organ is shown as a box split into two sub-compartments, the upper number denoting intravascular (capillary) volume and the lower number denoting extracellular fluid volume. The concentration of contrast agent in an organ is determined by the ratio of the total mass to the total volume of contrast agent within that organ. The total mass of contrast agent within an organ is calculated by summing the products of the concentrations and the volume in the intravascular and extracellular spaces. The organ volume is obtained by adding the intravascular (IV), extracellular (EC) and intracellular (IC) volumes.

A total of 104 ordinary differential equations were used to describe the cardiovascular model of the preferred embodiment. These equations were solved using the numerical integration programs of the fifth order Runge-Kutta method on a personal computer. Using a power Macintosh or IBM PC the computation took a few seconds to compute. The contrast concentration curve over time was calculated for each region by solving differential equations of the preferred embodiment for a given contrast injection protocol and a hypothetical patient with variable weight, height, gender and age.

Figure 6:
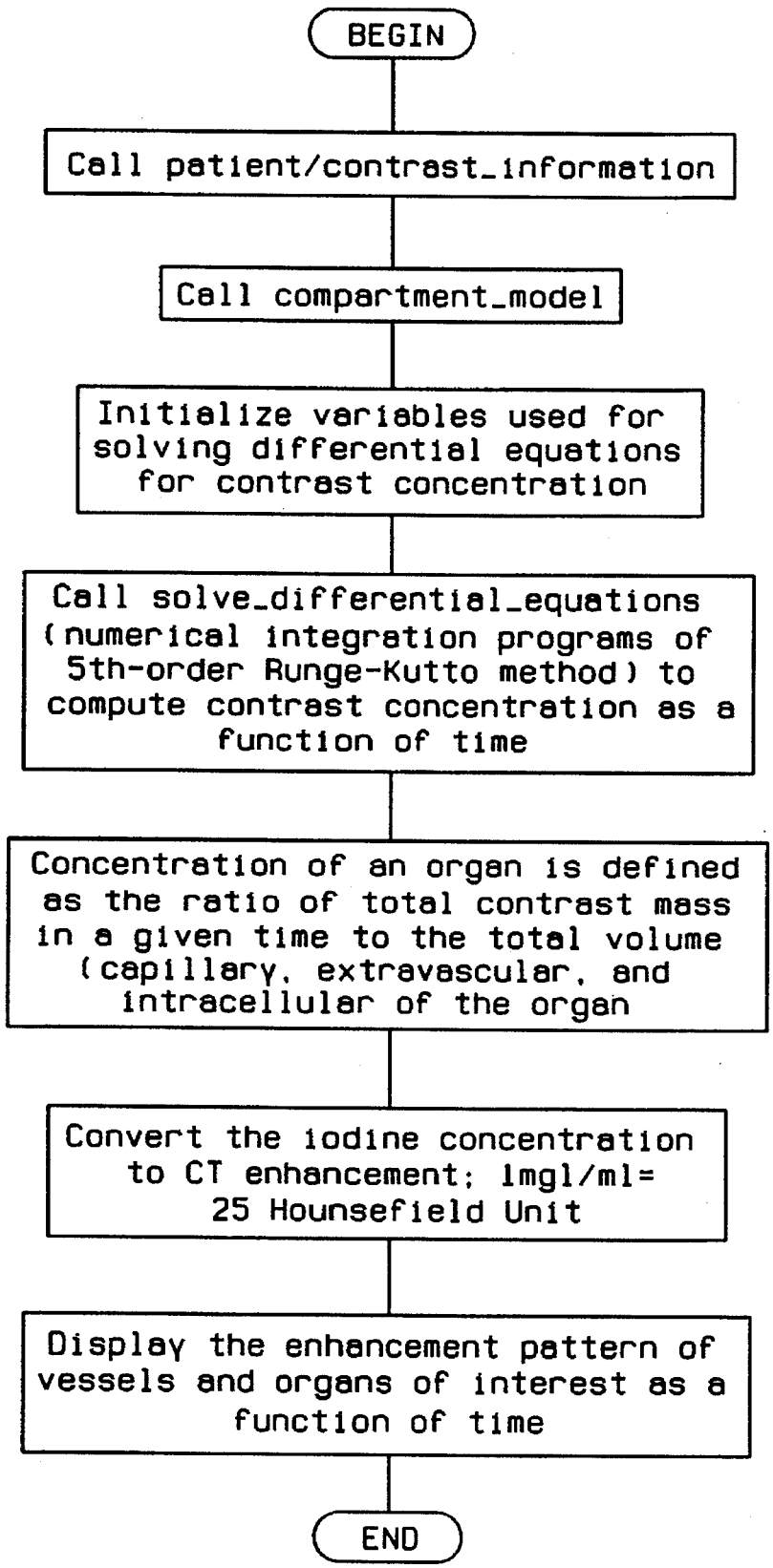
FIGS. 6 is a flow chart showing the method steps for determining predicted contrast enhancement level.
Figure 7:
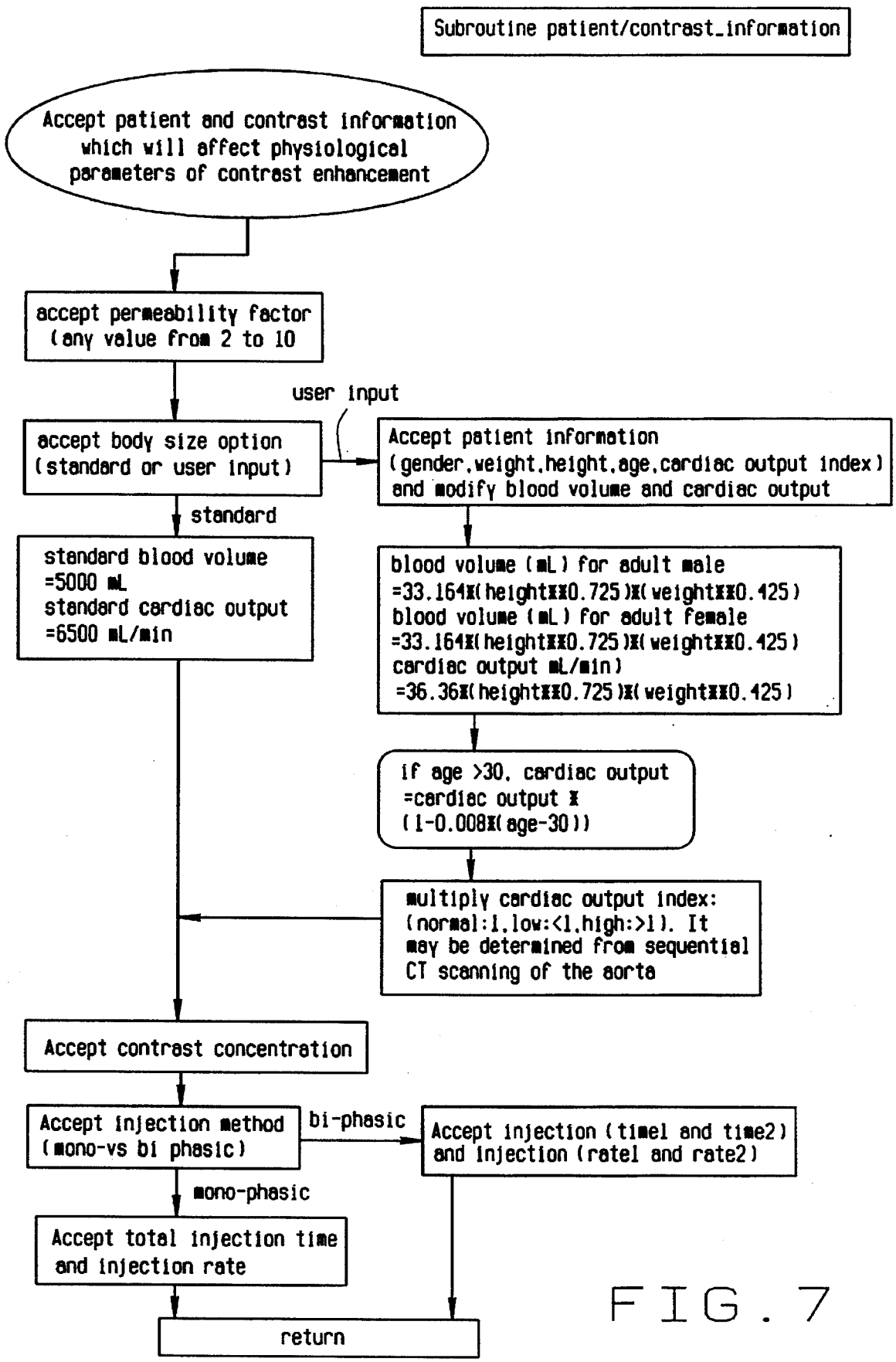
FIG. 7 is a flow chart of a subroutine of the method of FIG. 6 for operator designation of patient information and contrast protocol information.

Referring to FIG. 6, the method of the present invention is shown as a flow chart. The first step in the method is to call the patient/contrast information subroutine shown in FIG. 7. This subroutine accepts operator input of patient and contrast information which will affect physiological parameters of contrast enhancement. First, a permeability factor with a range from 2 to 10 is input. Guidance for selection of an appropriate permeability factor is given, infra. However, the inventor has found that acceptable results are achieved upon operator selection of any number between 2 and 10. Next, a body size option is input. At this point, the user has a choice to use a standard model which will include a 5,000 milliliter blood volume and standard cardiac output of 6500 ml/min or a user may input specific information. If specific information is input, the standard blood volume and standard cardiac output are adjusted to conform to the patient's specific information. Blood volume (BV) and cardiac output (CO) can be predicted from the weight (W) in pounds and height (H) in inches of a patient using regression formulae available in standard cardiovascular physiology references. The formula for an adult male with a weight (W) ranging from 100 to 310 pounds, and a height (H) ranging from 60 to 74 inches is:

$$BV=33.164*H^{0.725}*W^{0.425}-1229.$$

For an adult female with weight (W) ranging from 80 to 290 pounds and height (H) ranging from 60 to 74 inches the formula is:

$$BV=34.85*H^{0.725}*W^{0.425}-1954.$$

For an adult male or female, the cardiac output (CO) is given by the formula:

$$CO=36.36*H^{0.725}*W^{0.425}$$

In the preferred embodiment, an adjustment to these variables was made as follows. The ratio of the predicted blood volume to the standard blood volume was calculated. This ratio was then applied to the regional blood volume and extravascular fluid volume in the cardiovascular model so the entire body fluid volume was corrected. The cardiac output and regional blood flow were also modified in the same fashion. Consequently, the regional blood flow, blood volume, and distribution of body fluid in the model can be adjusted for subjects of different body weight, height, and gender.

Cardiac output can be further adjusted based on age using the formula:

$$CO=6500 \; ml/min*(1-0.008*(age-30)).$$

When inputting patient specific information, a choice can be made to further adjust the cardiac output for normal, low, and high. The cardiac output level can be estimated using sequential CT scanning of the aorta.

Figure 8:
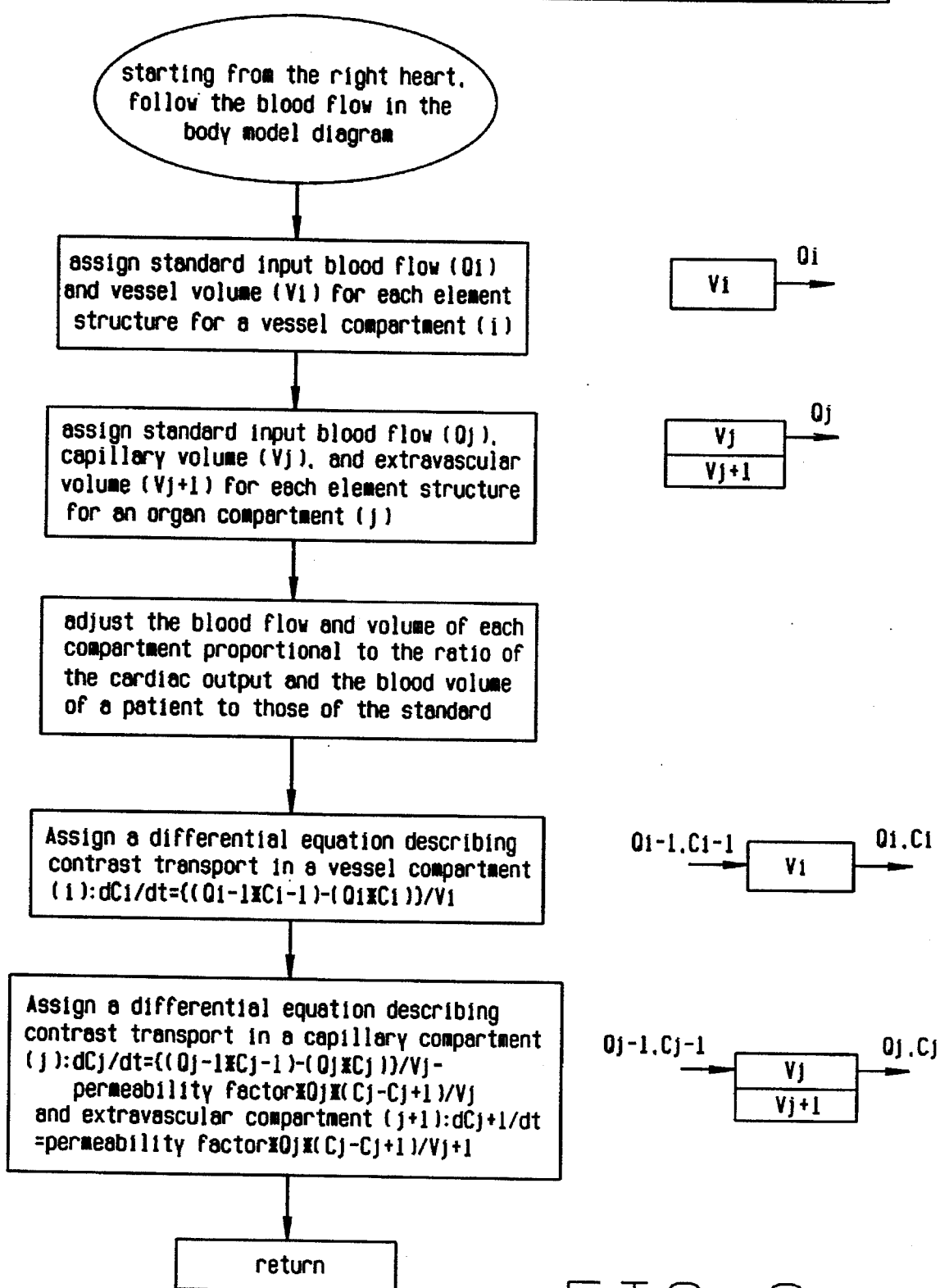
FIG. 8 is a flow chart of a subroutine of the method of FIG. 6 which assigns a differential equation to each element of the cardiovascular model.

Next, a contrast agent concentration is input and accepted as well as an injection method, total injection time, and injection rate. These values are all well known to those of ordinary skill in the art for particular types of CT scans. Thereafter, control is returned to the main program. The second step of the method is to call the compartment/model subroutine. This subroutine, shown in FIG. 8, begins with the right heart and follows the blood flow in the body model diagram shown in FIG. 5. A standard input blood flow and vessel volume is assigned sequentially for each circle element representing a vessel compartment in FIG. 5. Next, a standard input blood flow, a capillary volume, and an extravascular volume is assigned sequentially for each block element representing an organ compartment in FIG. 5. Thereafter, the blood flow and volume of each vessel and organ compartment is adjusted by the program to be proportional to the ratio of the cardiac output and blood volume of the patient as compared to the standard, as calculated in the patient/contrast subroutine.

In the next step, a differential equation describing the contrast agent transport in each vessel compartment, as derived above, is assigned. If the element is a vessel compartment, a differential equation describing contrast agent transport is assigned. If the element is an organ compartment, two differential equations describing both contrast agent transport in the intravascular compartment and in the extravascular compartment are assigned. Thus, each element in the cardiovascular system is assigned sequentially a differential equation. Control is then returned to the main program.

The next step in the method is to solve the differential equations which were assigned in the compartment/model subroutine to obtain the organ specific concentration. The differential equations are solved with numerical integration programs of the 5th-order Runge-Kutta method to compute contrast agent concentration as a function of time for each compartment.

The concentration of contrast agent in an organ is defined as the ratio of total contrast mass at a specific time to the total volume of the organ. Contrast concentration is converted to CT enhancement in Hounsefield Units (HU) using the ratio 1 milligram I/ml=25 HU. The relationship between CT enhancement in HU and concentration of contrast agent in mg/ml depends upon multiple factors including the type of contrast agent, the surrounding tissue and other factors related to the CT scanner such as peak kilovolts used ($kV_p$). The assumed relationship of 1 mg/ml equals 25 HU was arrived at through an experiment comparing CT attenuation and contrast concentration.

Figure 9:
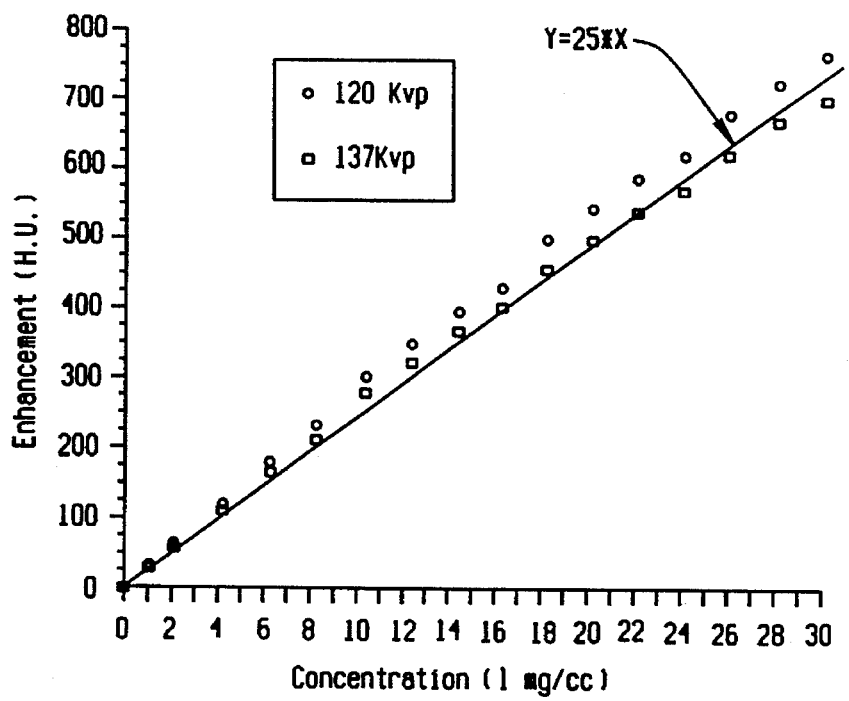
FIG. 9 is a graph showing the linear relationship between enhancement in Hounsefield Units (H.U.) and concentration of Iodine (I mg/ml)

In that experiment, Ioversol-320 (I) was diluted with saline to generate various concentrations ranging from 0 to 30 mg/ml. Fifty ml deposits of the solutions were placed in plastic jars and scanned with a Siemans Somatom Plus CT scanner using standard abdomen and chest settings of 120 $kV_p$ and 137 $kV_p$. CT attenuation was recorded by placing a 1.5 centimeter circular region of interest in the center of each jar on each image. Enhancement was computed as the difference between CT attenuation in each jar and the CT attenuation in a jar filled with normal saline. FIG. 9 is a graph showing the recorded enhancement levels ranging from 8 to 800 HU for concentrations ranging from 0 to 30 mgI/ml at each of 120 $kV_p$ and 137 $kV_p$. When a linear relationship was assumed, an increase in concentration by 1 mgI/ml yielded an approximate increase in contrast enhancement of 25 HU.

The last step in the method shown in FIG. 6 is providing a display of the enhancement pattern of the vessels and organs of interest as a function of time. This can be through either a data stream or a graph.

To gauge the accuracy of the present invention, simulated graphs were generated for a hypothetical patient using different injection protocols. These simulated graphs were compared to empiric graphs representing actual enhancement level measurements in patients who had undergone contrast enhanced CT scans. The empiric graphs represent an average of the recorded enhancement levels in the aorta and liver from three groups of 25 to 28 patients for the injection protocols listed in Table 6 below. Each injection consisted of 125 milliliters of Ioversol-320. The data used to create the empiric enhancement graphs was collected in an unrelated experiment regarding enhancement levels and both uniphasic and biphasic injection protocols. A biphasic injection uses two injection rates during the injection time. A uniphasic injection uses one injection rate during the injection time.

Figure 10A:
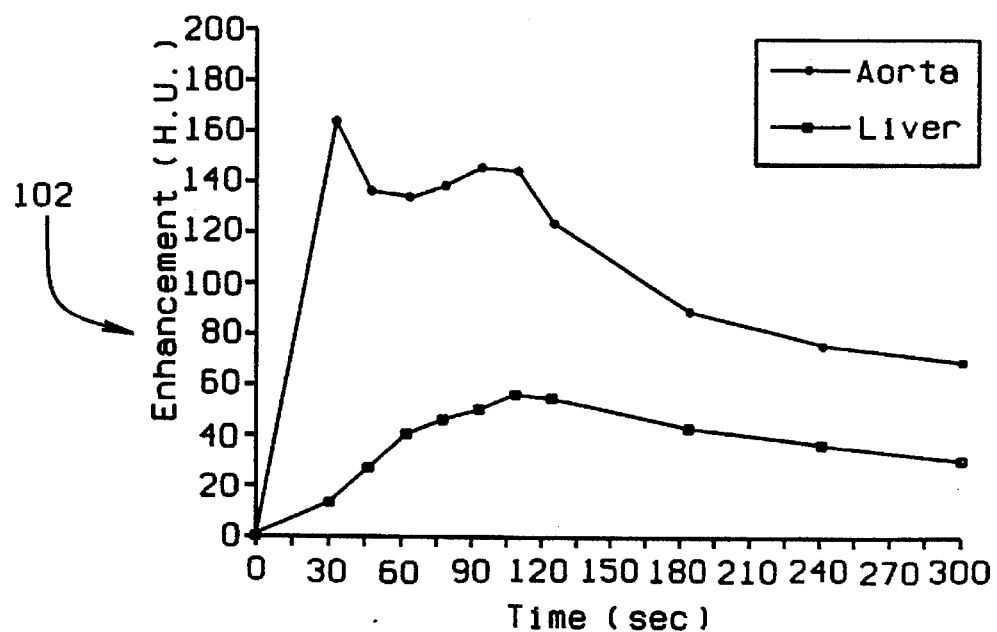
FIG. 10 is a graph showing simulated (10b) and empiric (10a) aortic and hepatic enhancement using the biphasic-low flow rate injection protocol given in Table 6.
Figure 10B:
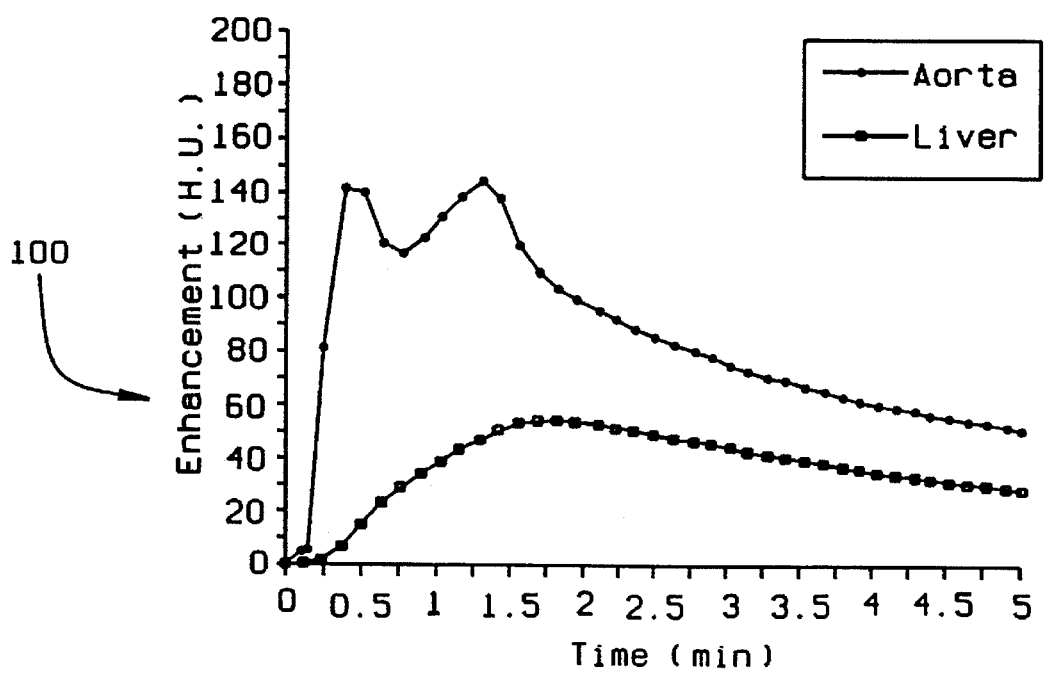

The simulated graphs represent contrast enhancement for each of the three protocols in Table 6 based on a hypothetical patient whose weight equalled the average weight of the corresponding empirical group of patients. Thus, each point on the empiric graphs represents an average of a wide range of empirical enhancement values while each point in the simulated graphs represents a single enhancement value for a hypothetical patient. FIG. 10 shows a simulated graph 100 and an empiric graph 102 for the biphasic-low flow rate injection protocol shown in Table 6. The hypothetical patient, whose enhancement levels are represented in the simulated graph 100, had an assumed body weight of 158 pounds. This assumed body weight was equal to the average body weight of the 28 patients whose actual mean enhancement levels are represented by the empiric graph 102.

Figure 11A:
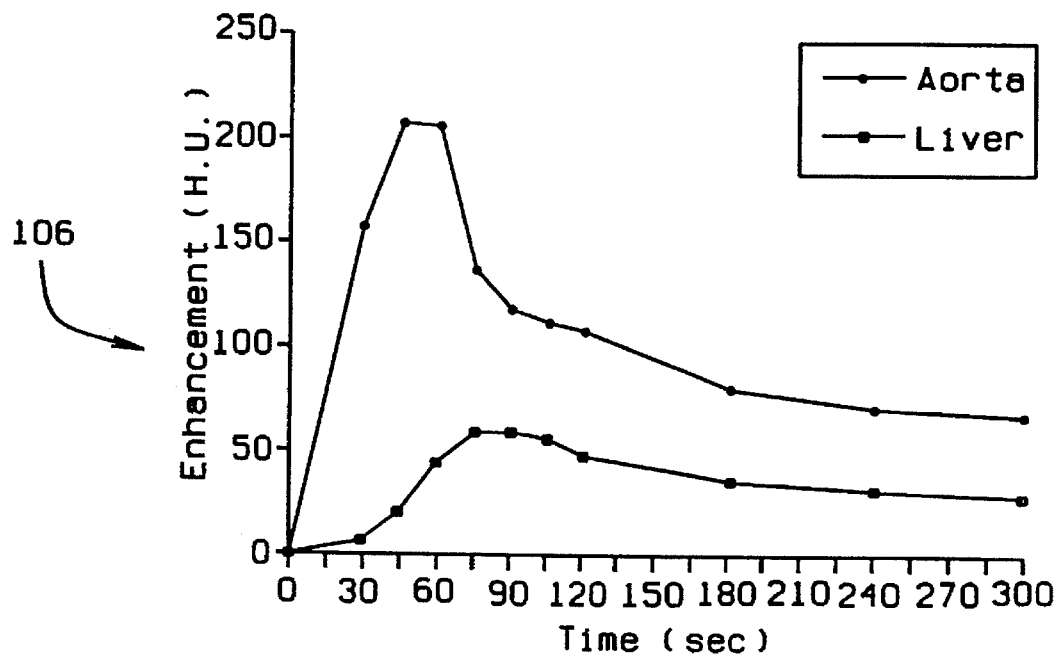
FIG. 11 is a pair of graphs showing simulated (11b) and empiric (11a) aortic and hepatic enhancement using the uniphasic-low flow rate injection protocol given in Table 6.
Figure 11B:
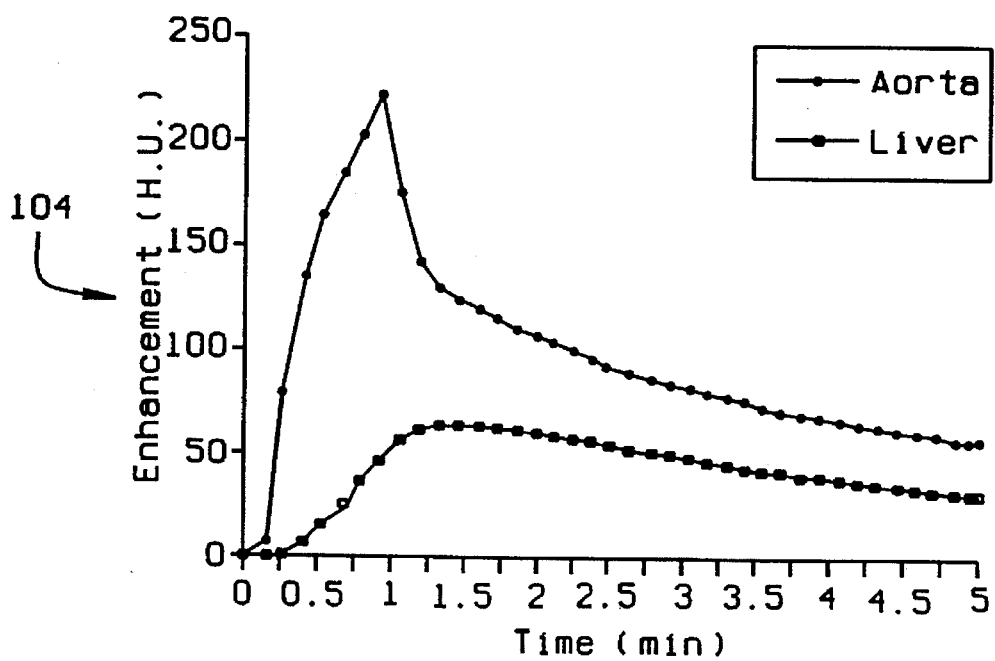

FIG. 11 shows a simulated graph 104 and an empiric graph 106 for the uniphasic-low flow rate injection protocol in Table 6. The hypothetical patient, whose enhancement levels are represented in the simulated graph 104, had an assumed body weight of 171 pounds. This assumed body weight was equal to the average body weight of the 25 patients whose actual mean enhancement levels are represented by the empiric graph 106.

Figure 12A:
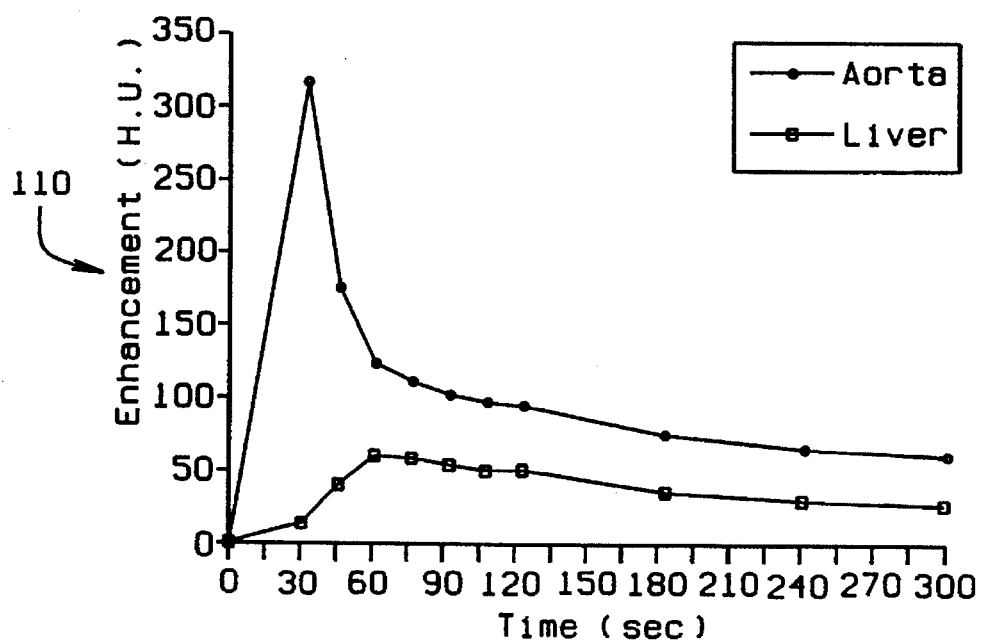
FIG. 12 is a graph showing simulated (12b) and empiric (12a) aortic and hepatic enhancement using the uniphasic-high flow rate injection protocol given in Table 6.
Figure 12B:
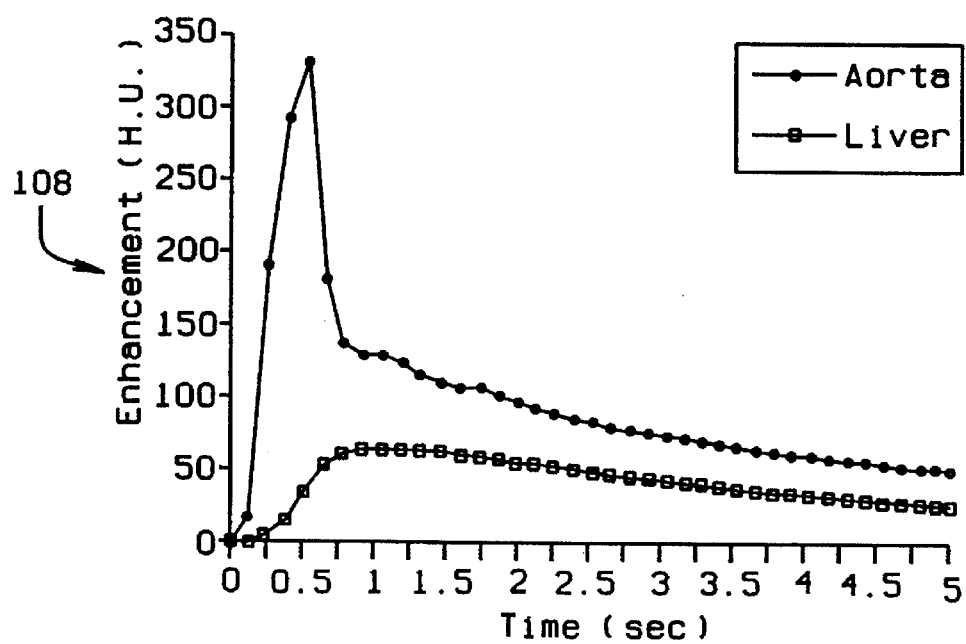

FIG. 12 shows a simulated graph 108 and an empiric graph 110 for the uniphasic-high flow rate injection protocol in Table 6. The hypothetical patient, whose enhancement levels are represented in the simulated graph 108, had an assumed body weight of 177 pounds. This assumed body weight was equal to the average body weight of the 27 patients whose actual mean enhancement levels are represented by the empiric graph 110.

The simulated and empirical contrast enhancement graphs were compared according the maximum enhancement level of each graph and the percent difference between the graphs. The simulated graphs were in good agreement with the empiric graphs. For example, in FIG. 10, for the biphasic-low flow rate injection protocol the simulated maximum aortic enhancement was 142.7 HU while the empiric maximum aortic enhancement was 163.4 HU. Also in FIG. 10, the simulated maximum hepatic enhancement was 53.8 HU while the empiric maximum hepatic enhancement was 55.5 HU.

In FIG. 11, for the uniphasic-low flow rate injection protocol, the simulated maximum aortic enhancement was 220.4 HU while the empiric maximum aortic enhancement was 205.8 HU. Also in FIG. 11. the simulated maximum hepatic enhancement was 63.8 HU while the empiric maximum hepatic enhancement was 59.8 HU.

In FIG. 12, for the uniphasic-high flow rate injection protocol the simulated maximum aortic enhancement was 321.3 HU while the empiric maximum aortic enhancement was 313.7 HU. Also in FIG. 12, the simulated maximum hepatic enhancement was 63.6 HU while the empiric maximum hepatic enhancement was 60.8 HU.

The total mean difference in maximum enhancement between the simulated and empiric graphs was 7.4 percent for aortic enhancement and 4.8 percent for the hepatic enhancement. As can be seen in FIGS. 10, 11 and 12, the simulated and empiric graphs were also nearly identical in variation over time. Specifically, the average enhancement difference between the simulated and empiric graphs for all three protocols in Table 6 was 11.6 percent for aortic enhancement and 12.7 percent for hepatic enhancement.

Figure 13A:
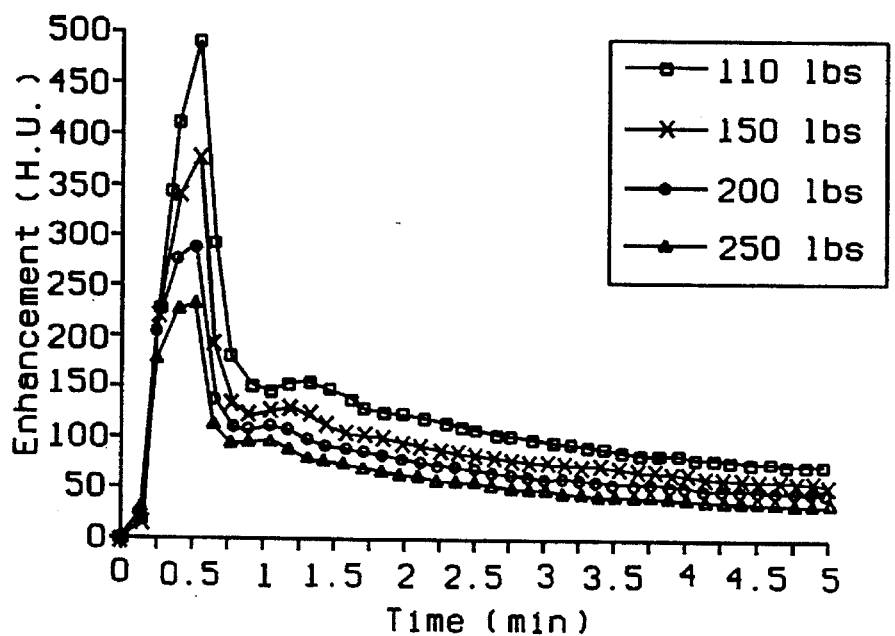
FIG. 13 is a graph showing simulated aortic and hepatic enhancement curves generated by the present invention for hypothetical patients weighing 110, 150, 200 and 250 pounds.
Figure 13B:
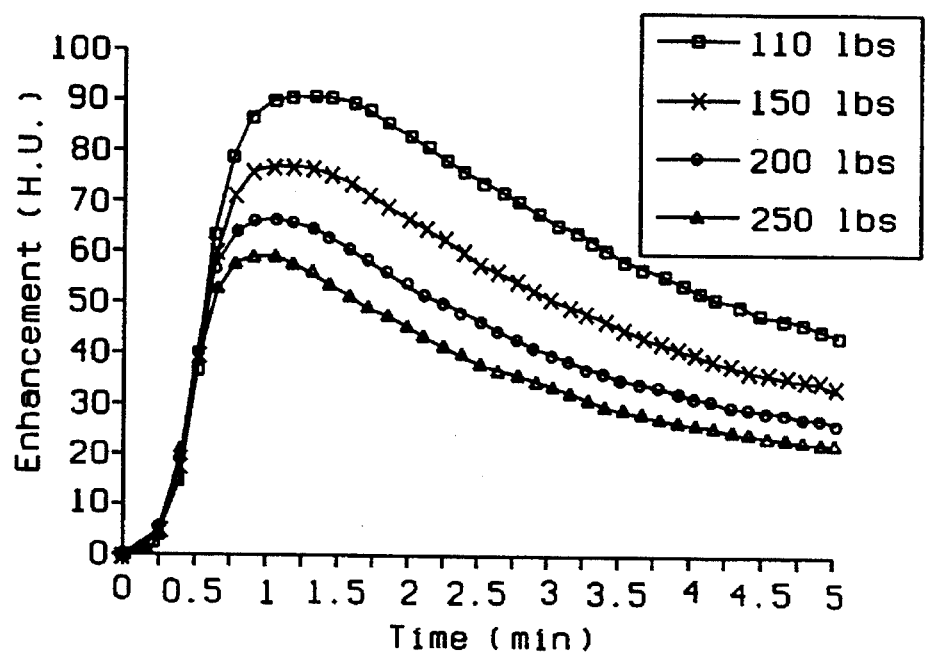

It is well known that body weight is one of the patient variables which most drastically affects contrast enhancement. To confirm the functionality of the present invention, the effect of body weight on contrast enhancement was simulated in a hypothetical patient. FIG. 13(a) shows simulated aortic enhancement graphs and FIG. 13(b) shows simulated hepatic enhancement graphs for uniphasic-high injection protocol in an adult male with a fixed height (5'8") and body weights of 110, 150, 200 and 250 pounds. The simulated graphs demonstrate that contrast enhancement was greatly effected by body weight. For example, in FIG. 13(a), the peak aortic enhancement in a subject weight 110 pounds was more than twice that in a subject weighing 250 pounds. However, as expected, the timing of the aortic and hepatic peaks did not vary significantly because alteration in the cardiac output was compensated by alteration in the blood and body fluid volume. The simulated graphs in FIG. 13 correlate well with empiric observations in patients showing an inverse relationship between body weight and contrast enhancement.

In the patient/contrast subroutine, selection of a permeability factor between 2 and 10 is required, as explained, infra. However, of the variables used to construct the cardiovascular model of the present invention, the least is known about the transcapillary permeability. Permeability varies from organ to organ and depends, in part, on the substance being transferred. Organs with discontinuous capillaries such as the liver, spleen and bone marrow have relatively high permeability. Fenestrated capillaries in the kidney and intestines have intermediate permeability. Continuous capillaries in the heart muscle and skin have smaller pores and thus lower permeability.

Although some general information about permeability is known, knowledge about specific transcapillary permeability is limited. For example, the size of the contrast substance is one of the most important properties in determining the rate of transcapillary exchange. Permeability for different substances will vary according to each substance's molecular weight. Most nutrients and metabolites including glucose (mw=180) and sucrose (mw=342) are quite readily diffusible.

When transcapillary exchange occurs slowly relative to the blood flow rate, it is primarily diffusion-limited. Conversely, if transcapillary exchange occurs rapidly relative to the blood flow rate, it is primarily flow-limited. Iodinated contrast agents consist of relatively small molecules with molecular weights between 800 and 1600. Such contrast agents are distributed rapidly and extensively outside the blood vessels to the entire extracellular fluid within a few minutes of injection and are highly diffusible. Therefore, in the present invention, it was assumed that the transport of contrast agents to be mostly flow-limited and this assumption was applied equally to every organ in the cardiovascular model.

Figure 14A:
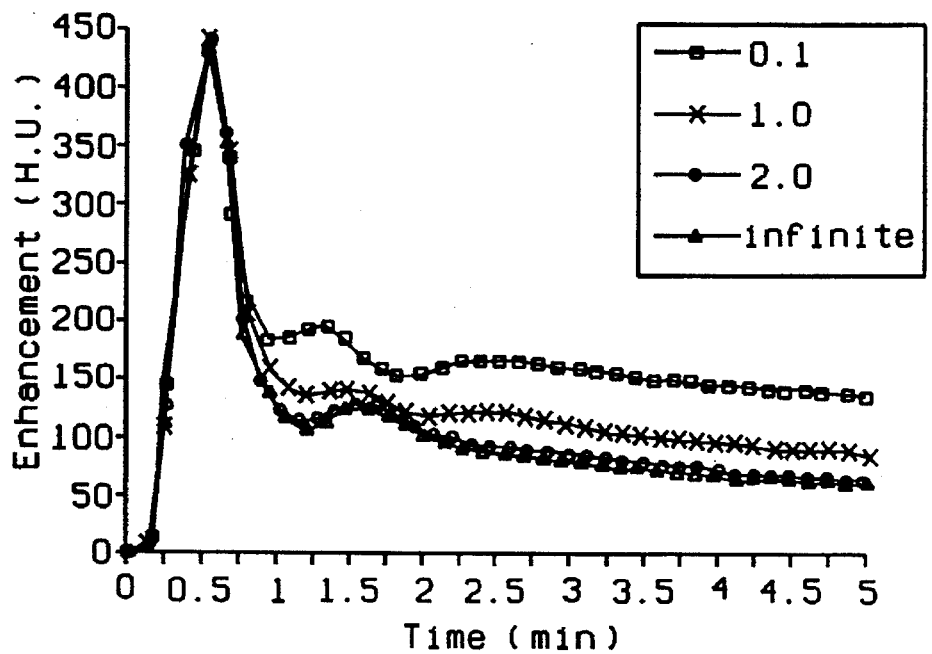
FIG. 14 is a graph showing simulated aortic (14a) and hepatic (14b) enhancement curves for permeability (PS) values of 0.1, 1.0, 20 and infinity.
Figure 14B:
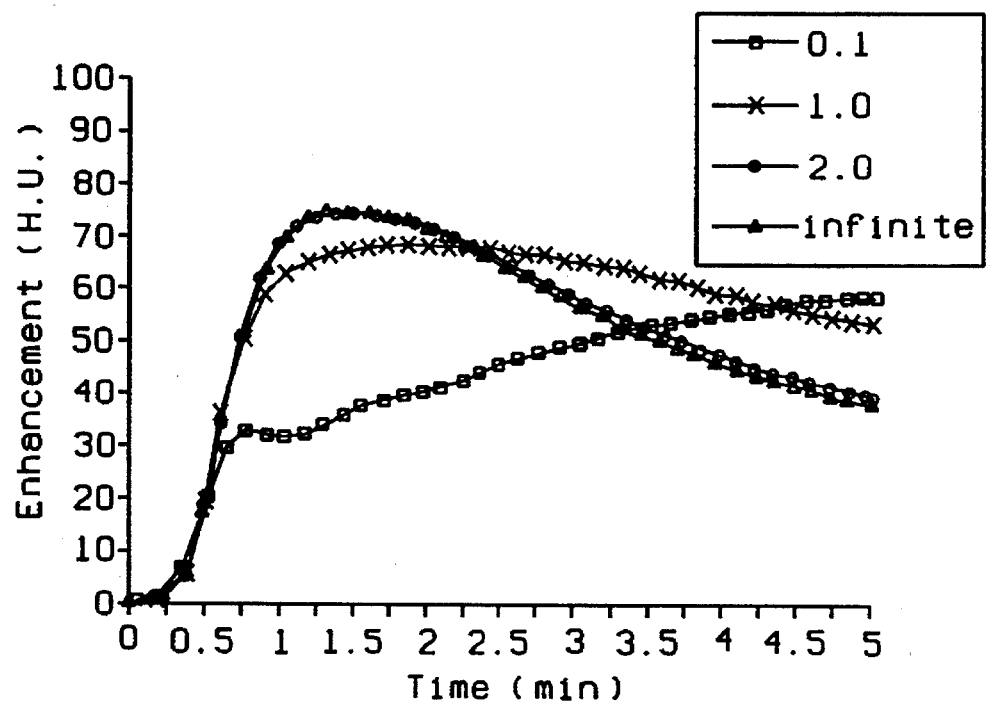

Permeability (P) and transfer area (S) are usually treated as a unit because of the difficulty evaluating them separately without very detailed anatomical information. The permeability-surface area product (PS) is referred to as the "capillary transport coefficient." The magnitude of PS in an organ is frequently expressed relative to the blood flow rate, Q. If PS/Q is larger than 1, the transport is flow-limited. If PS/Q is less than 1, it is diffusion-limited. In an effort to determine acceptable PS values in the present invention, simulated CT enhancement graphs were generated for several different PS/Q values. The simulated graphs are shown in FIG. 14(a) for aortic and FIG. 14(b) for hepatic for PS/Q values equal to 0.1, 1, 2, 20 and infinity.

Simulated graphs were also generated assuming no transcapillary barrier between the capillary and extracellular spaces, i.e., a single compartment representing each organ. The simulated CT enhancement graphs generated by the present invention with PS/Q=20 closely approach those obtained by ignoring the transcapillary barrier. Thus, this PS/Q value is near the upper limit of flow-limited capillary transport. The simulated graphs shown in FIGS. 14(a) and 14(b), when compared with empiric graphs, confirm that the transport of contrast agent follows a flow-limited process, especially in richly perfused tissues.

Figure 16:
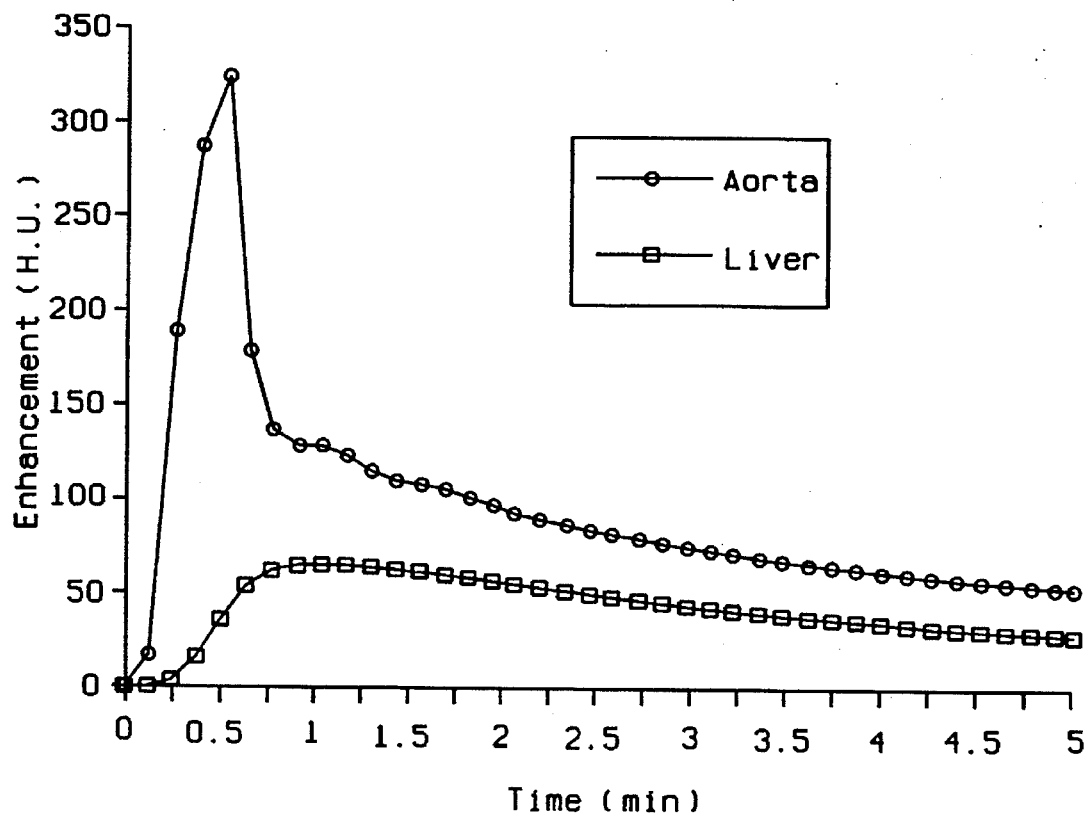
FIG. 16 is a graph output generated by the present invention showing predicted aortic and hepatic enhancement levels versus time using the data in FIG. 15.

FIGS. 15 and 16 show sample aortic and hepatic enhancement levels generated by the present invention in data format and graph format, respectively. Operation of the present invention can be best understood by referring to FIG. 15. Prior to performing a CT scan, an operator inputs the patient specific information, such as height weight and cardiac output, and an injection protocol into the program in accordance with the above description of the preferred embodiment. The program then generates output data showing the predicted organ specific enhancement values as a function of time. The output data can take the form of a data stream as shown in FIG. 15 or a graph as shown in FIG. 16.

The operator views the data initially to determine whether the proposed injection protocol will result in an acceptable enhancement level for an acceptable duration. If the data shows that the desired enhancement level will never be reached, or will not be sustained for a sufficient length of time, the operator chooses a different injection protocol and then reruns the program until a satisfactory predicted enhancement level is obtained.

After the operator obtains an output showing an acceptable predicted enhancement level and duration, the operator then selects a scan start time and duration, including an appropriate collimation thickness and table speed. In the alternative, all or a portion of the selection can be performed by the computer. This information is then input into the CT scanner, if obtained off-line from the CT control computer, and the scan is then executed.

For example, assuming a threshold hepatic enhancement level of 50, the data of FIG. 15 shows that the threshold enhancement level is not reached until 0.64 minutes after the injection of contrast agent into the patient. In addition, the data shows that the threshold enhancement level will be maintained for approximately 1.7 minutes. Using this information, an operator inputs the scan start time, scan duration, collimation thickness and table speed into the CT scanner and thereafter performs the scan on the patient. In the alternative, computer software can be implemented to automatically transmit the output information directly into the CT scanner.

There are various changes and modifications which may be made to the invention as would be apparent to those skilled in the art. However, these changes or modifications are included in the teaching of the disclosure, and it is intended that the invention be limited only by the scope of the claims appended hereto.

TABLE 1

Estimated distribution of blood in vascular system of an adult human

|  | Volume | |
| --- | --- | --- |
| Region | mL | % |
| Heart (diastole) | 360 | 7.2 |
| Pulmonary | 440 | 8.8 |
| Arteries | 130 | 2.6 |
| Capillaries | 150 | 3.0 |
| Veins | 160 | 3.2 |
| Systemic | 4,200 | 84 |
| Aorta and large arteries | 300 | 6.0 |
| Small arteries | 400 | 8.0 |
| Capillaries | 300 | 6.0 |
| Small veins | 2,300 | 46.0 |
| Large veins | 900 | 18.0 |
| Total | 5,000 | 100 |

Modified from the reference [Milnor].

TABLE 2

Estimated distribution of cardiac output in an adult human. The liver receives dual blood supplies, hepatic artery and portal system.

| Region | Blood flow mL/min | % |
|---|---|---|
| Upper extremities | 325 | 5.0 |
| Head | 975 | 15.0 |
| Coronary | 260 | 4.0 |
| Bronchial | 130 | 2.0 |
| Kidneys | 1,430 | 22.0 |
| Liver | 1,885 | 29.0 |
| Hepatic artery | 455 | 7.0 |
| Portal | 1,430 | 22.0 |
| Spleen/stomach | 430 | 6.6 |
| Pancreas/Intestine | 1000 | 15.4 |
| Trunk/Lower Extrem. | 1,495 | 23.0 |
| Total | 6,500 | 100 |

Modified from reference [wade].

TABLE 3

Estimated distribution of body fluid in an adult human

| compartment | volume (liter) |
|---|---|
| ICF (except RBC) | 19.1 |
| ECF (except plasma) | 15.9 |
| Blood (plasma + RBC) | 5.0 |
| Total body water | 40 |

Estimation based on the volume of distribution of iohexol [Olsson].

TABLE 4

Estimated distribution of % blood flow rate and capillary volume in an adult human. Regional capillary volume is calculated proportional to a regional blood flow of the total 122% (the portal system contributes additional 22%).

| Region | Blood flow % | Capillary Volume mL |
|---|---|---|
| Upper extremities | 5.0 | 12 |
| Head | 15.0 | 37 |
| Coronary | 4.0 | 10 |
| Bronchial | 2.0 | 5 |
| Kidneys | 22.0 | 54 |
| Liver | 29.0 | 71 |
| Spleen/stomach | 6.6 | 16 |
| Pancreas/Intestine | 15.4 | 38 |
| Trunk/Lower Extrem. | 23.0 | 57 |
| Total | 100 (122) | 300 |

TABLE 5

Estimated weight, water content, and fluid volume of visceral organs in a 70 Kg adult. The lung consists of 50% parenchyma and 50% non-parenchyma tissues whose capillary volumes are 150 mL and 5 mL, respectively.

| organ | weight (g) | % water | Fluid (mL) | Fluid-cap. |
|---|---|---|---|---|
| Brain | 1,450 | 76 | 1102 | 1065 |
| Heart | 300 | 79 | 237 | 227 |
| Lung | 500 + 500 | 79 | 790 | 635 |
| Kidneys | 300 | 83 | 249 | 195 |
| Liver | 1,800 | 68 | 1224 | 1153 |
| Spl./Stomach | 170/150 | 70 | 224 | 208 |
| Panc./Intest. | 60/1,770 | 70 | 1281 | 1243 |
| Total | 7,000 | | 5,107 | 4,726 |

Modified from references [ICRP, Mapleson].

TABLE 6

Tested Injection Protocols

| Protocol | First Rate (mL/sec) | First Rate Volume (mL) | Second Rate (mL/sec) | Second Rate Volume (mL) | Injection Time (sec) | Number of patient | Mean (range) of weight (lb.) |
|---|---|---|---|---|---|---|---|
| Biphasic-low | 2.5 | 50 | 1 | 75 | 95 | 28 | 158 (100–205) |
| Uniphasic-low | 2.5 | 125 | — | — | 50 | 25 | 171 (108–241) |
| Uniphasic-high | 5.0 | 125 | — | — | 25 | 27 | 177 (98–300) |

What is claimed is:

1. A method of scanning a tissue in a patient using computed tomography, said patient having a plurality of patient specific parameters, wherein the tissue to be scanned is enhanced with an intravascularly injected contrast agent, comprising the steps of:

selecting an injection protocol for the contrast agent;

predicting, using a mathematical model, prior to implementing said injection protocol a tissue enhancement level as a function of an elapsed time after injection based on the injection protocol and said patient specific parameters;

determining a set of parameters for an optimum scan based on the predicted tissue enhancement level; and performing the scan in accordance with the pre-determined set of optimum scan parameters.

2. The method of claim 1 wherein the step of predicting the tissue enhancement level comprises the steps of:

providing a mathematical model which describes contrast agent transport throughout the patient's cardiovascular system;

inputting into the mathematical model as said patient specific parameters patient specific information and contrast agent specific information which affects physiological parameters of contrast enhancement; and using the mathematical model to compute a contrast agent concentration as a function of time.

3. The method of claim 2 wherein the step of providing a mathematical model includes the steps of:

providing a compartmental model of the human cardiovascular system including vessel compartments representing blood vessels and organ compartments representing organs;

assigning at least one differential equation describing contrast agent transport to each vessel compartment; and assigning at least one differential equation describing contrast agent transport to each organ compartment.

4. The method of claim 3 further comprising the steps of:

assigning a standard input blood flow and a standard vessel volume for each vessel compartment;

assigning a standard input blood flow, a standard capillary volume, and a standard extravascular volume for each organ compartment;

adjusting the standard input blood flow of each vessel compartment and each organ compartment as being proportional to a ratio of cardiac output of the patient to a standard cardiac output; and adjusting the standard capillary volume and the standard extravascular volume of each organ compartment as being proportional to the ratio of blood volume of the patient to a standard blood volume.

5. The method of claim 4 wherein each organ compartment is further subdivided into a capillary compartment and an extravascular compartment and the step of assigning at least one differential equation to each organ compartment includes assigning at least one differential equation to each capillary compartment and each extravascular compartment.

6. The method of claim 2 wherein the inputting step includes the steps of:

inputting a permeability factor;

inputting a patient habitus;

inputting a patient blood volume;

inputting a patient cardiac output;

inputting a contrast concentration value;

inputting an injection method;

inputting an injection time; and inputting an injection rate.

7. The method of claim 6 wherein the step of inputting a patient habitus includes inputting the patient's age, gender, weight, and height.

8. The method of claim 7 wherein the step of inputting the patient blood volume includes the step of computing the patient's blood volume.

9. The method of claim 8 wherein the step of inputting the patient cardiac output includes the steps of calculating a standard cardiac output and adjusting the standard cardiac output proportional to a ratio of a cardiac output of the patient to a standard cardiac output.

10. The method of claim 2 further comprising the steps of:

converting the computed contrast agent concentration into the tissue enhancement level as expressed in computed tomography enhancement units; and displaying the tissue enhancement level in computed tomography enhancement units as a function of time.

11. A method for predicting a tissue enhancement level as a function of time for a specific tissue in a patient receiving an intravascularly injected contrast agent via a specified injection protocol, said method comprising the steps of:

providing a mathematical model of the cardiovascular system of the patient, said model mathematically describing the transport of said contrast agent through said cardiovascular system, inputting into said model a plurality of patient specific parameters which impact the transport of said contrast agent, using said model to calculate a predicted concentration of said contrast agent in said tissue as a function of time in response to said specified injection protocol, and displaying said predicted contrast agent concentration as a function of time as representative of said tissue enhancement level as a function of time.

12. The method of claim 11 further comprising the step of inputting a set of parameters into said model corresponding to said specified injection protocol, said predicted concentrations being responsive thereto.

13. The method of claim 12 further comprising the step of comparing a minimum threshold value with said tissue enhancement level to thereby determine a start time and time duration of acceptable tissue enhancement level during which a CT scan may be taken.

14. The method of claim 13 wherein said mathematical model comprises a plurality of compartments representative of significant organs and vessels in said cardiovascular system, each of said compartments being characterized by at least one differential equation.

15. The method of claim 14 wherein said mathematical model is embodied in a computer program.

16. A computer being programmed for predicting a structure specific CT enhancement level in a patient for a given patient habitus and a specific contrast injection protocol comprising:

a computer having a memory;

a computer program in said memory, said program having means for accepting patient specific information and contrast specific information which affect physiological parameters of contrast enhancement and means for computing and outputting operator selected organ specific contrast concentration as a function of time.

17. The computer of claim 16 wherein the means for computing organ specific contrast concentration comprises a mathematical compartmental model of the human cardiovascular system including vessel compartments representing blood vessels and organ compartments representing organs;

at least one differential equation describing contrast transport to each vessel compartment; and at least one differential equation describing contrast transport to each organ compartment.

18. The computer of claim 17 wherein said computer program further comprises:

means for assigning a standard input blood flow and standard vessel volume for each vessel compartment;

means for assigning a standard input blood flow, a standard capillary volume, and a standard extravascular volume for each organ compartment;

means for adjusting the standard input blood flow of each vessel compartment and each organ compartment as being proportional to a ratio of cardiac output of the patient to a standard cardiac output;

means for adjusting the standard capillary volume and the standard extravascular volume of each organ compartment as being proportional to the ratio of blood volume of the patient to a standard blood volume.

19. The computer of claim 18 wherein said computer program further comprises means for further subdividing each organ into a capillary compartment and an extravascular compartment and the step of assigning at least one differential equation to each organ compartment includes assigning at least one differential equation to each capillary compartment and each extravascular compartment.

20. The computer of claim 19 wherein said computer program further comprises means for converting the computed contrast concentration into computed tomography enhancement units and means for displaying the enhancement level of the organ in computed tomography enhancements units as a function of time.

21. A computed tomography machine comprising:

a computed tomography machine;

a computer having a memory connected to said computed tomography machine for controlling its operation; and a computer program in said computer memory, said computer program having means for predicting a structure specific CT enhancement level in a patient for a given patient habitus and a specific contrast injection protocol.

22. The computed tomography machine of claim 21, wherein said computer program comprises:

means for predicting prior to implementing an injection protocol an organ enhancement level as a function of time elapsed after implementing the injection protocol based on the injection protocol and patient specific parameters;

means for determining an optimum scan start time and scan duration based on the predicted enhancement level; and means for performing the scan in accordance with the pre-determined scan start time and scan duration.

* * * * *